United States Patent [19]
McEntire et al.

[11] Patent Number: 4,483,997
[45] Date of Patent: Nov. 20, 1984

[54] OLEFIN EPOXIDATION WITH INORGANIC METAL PHOSPHATE ENHANCED CATALYST

[75] Inventors: Edward E. McEntire; Robert M. Gipson, both of Austin, Tex.

[73] Assignee: Texaco Inc., White Plains, N.Y.

[21] Appl. No.: 462,250

[22] Filed: Jan. 31, 1983

[51] Int. Cl.$^3$ ............................................ C07D 301/19
[52] U.S. Cl. .................................................... 549/529
[58] Field of Search ......................................... 549/529

[56] References Cited

U.S. PATENT DOCUMENTS 3,526,645  9/1970  Vangermain et al. ............... 549/529
3,843,694 10/1974  Chremos et al. ..................... 549/529
3,870,729  3/1975  Bost et al. ............................ 549/529

FOREIGN PATENT DOCUMENTS 2231374  9/1973  Fed. Rep. of Germany .
3027349  2/1981  Fed. Rep. of Germany .
1393284  5/1975  United Kingdom ................ 549/529

OTHER PUBLICATIONS

F. Mashio et al., Mem. Fac. Ind. Arts Kyoto Tech. Univ., Sci. Technol. No. 16, (1967), pp. 79-91.
Venturello et al., Chemical Abstracts, vol. 95, (1981), 42876g.
Forzatti et al., La Chimica E L'Inudstria, vol. 56, No. 4, Apr. 1974, pp. 259-263.

Primary Examiner—Norma S. Milestone
Attorney, Agent, or Firm—Robert A. Kulason; Kenneth R. Priem; David L. Mossman

[57] ABSTRACT

A method for the preparation of an epoxide by reacting an olefin having 3 or more carbon atoms with a hydroperoxide in the presence of a catalyst. The catalyst includes molybdenum and/or tungsten and an inorganic metal phosphate and/or arsenate wherein at least the inorganic metal phosphate and/or arsenate is substantially insoluble in the olefin hydroperoxide reaction mixture. The metal portion of the inorganic metal phosphate and/or arsenate is one or more metals selected from the group consisting of the metals found in Groups I to III, VIIb and VIII, of the Periodic Table of Elements. Preferred metals include aluminum, iron, zinc and mixtures of these metals.

13 Claims, No Drawings

OLEFIN EPOXIDATION WITH INORGANIC METAL PHOSPHATE ENHANCED CATALYST

BACKGROUND OF THE INVENTION

1. Field of the Invention

This invention relates to the epoxidation of olefins and more particularly, to the use of inorganic phosphates as catalyst enhancers.

2. Description of the Prior Art

Epoxidation of ethylene can be rather simply and easily done on a commercial scale. However, epoxidation of higher olefins beginning with propylene is much more difficult to accomplish on a commercial scale. Previously, this had been done by a complicated chlorohydrin process and more recently, through the use of a soluble metal catalyst such as disclosed in U.S. Pat. Nos. 3,351,635 and 3,350,422. After the discovery of the catalytic effect of the soluble metal catalyst, a search was begun for methods of improving the catalytic activity of such metals. This search has concentrated on both soluble and insoluble forms of the metal catalyst.

German Pat. No. 2,231,374 sets forth an insoluble catalyst for the reaction of olefins with hydroperoxides to yield epoxides. The catalyst consist either of compounds of the elements of Groups IV to VI of the secondary system of the periodic system with tin, phosphorous, arsenic, antimony, bismuth, selenium and/or tellurium or of mixtures of these compounds, or of mixtures of compounds of the elements of the secondary Groups IV to VI and the elements of the main groups IV to VI.

U.S. Pat. No. 3,526,645 sets forth the epoxidation of olefins using a compound of a metal selected from Groups IV, V and VI of the periodic table of elements mixed with a compound of a metal selected from Groups VII and VIII of the periodic table of elements.

U.S. Pat. No. 3,843,694 sets forth the use of boron phosphate to catalyze the oxidation of ethylenically unsaturated organic compounds to oxiranes with the use of an organic hydroperoxide.

U.S. Pat. No. 3,870,729 sets forth a process for the epoxidation of an olefinic compound by contacting the compound with an organic hydroperoxide in the presence of a soluble titanium compound and a phosphoric acid ester.

German Pat. No. 2,446,830 dated Apr. 3, 1975 (Chemical Abstracts 83, 58637t) sets forth a process for the epoxidation of olefins using hydrogen peroxide and a catalyst, one of the catalyst includes a lead phosphate.

Japanese Pat. No. 74 45,843 dated Dec. 6, 1974 (Chemical Abstracts 82, 171686a) sets forth the epoxidation of propylene to propylene oxide using an alkali metal phosphate and oxygen under high pressure and temperature.

SUMMARY OF THE INVENTION

A method for the preparation of an epoxide has been discovered which comprises the step of reacting an olefin having 3 or more carbon atoms with a hydroperoxide in the presence of a catalyst, which catalyst comprises molybdenum and/or tungsten and an inorganic metal phosphate and/or arsenate wherein at least the metal phosphate and/or arsenate is substantially insoluble in the olefin-hydroperoxide mixture. The molybdenum and/or tungsten can either be soluble or substantially insoluble in the olefin-hydroperoxide reaction mixture with at least the inorganic metal phosphate and/or arsenate being substantially insoluble in the olefin-hydroperoxide reaction mixture. By substantially insoluble it is meant that insufficient molybdenum, and/or tungsten or metal phosphate and/or arsenate dissolves into the reaction mixture so that when the insoluble portion of the catalyst is removed from the reaction mixture, the reaction does not proceed at a commercially significant rate, and that the presence of the insoluble metal phosphate and/or arsenate is required for the reaction to proceed at a commercially significant rate. Such a concentration of dissolved molybdenum and/or tungsten can be 100 parts per million, or lower than 10 parts per million. The metal of the inorganic metal phosphate is selected from the group consisting of the metals of Groups I to III, VIIb, and VIII of the periodic table of elements. It has been found that the presence of the substantially insoluble inorganic metal phosphate and/or arsenate enhances the catalytic activity of the soluble or substantially insoluble molybdenum and/or tungsten.

DESCRIPTION OF THE PREFERRED EMBODIMENTS

The catalyst composition employed in the preparation of an epoxide in the process of the present invention comprises molybdenum and/or tungsten, generally as a compound which is either soluble or substantially insoluble in the reaction mixture of the olefin and hydroperoxide, and a substantially insoluble inorganic metal phosphate and/or arsenate. The presence of the inorganic metal phosphate and/or arsenate enhances the catalytic activity of the molybdenum and/or tungsten whether it is soluble or not. When soluble molybdenum and/or tungsten is used, it can be conventionally dissolved in the reaction mixture and the insoluble inorganic metal phosphate added. When substantially insoluble molybdenum and/or tungsten is used, it is supported on and/or combined with the substantially insoluble inorganic metal phosphate and/or arsenate and this substantially insoluble catalyst is added to the reaction mixture. Effective insoluble catalysts are preferred since they can be readily removed from the reaction mixture after the epoxidation process is completed.

The substantially insoluble inorganic metal phosphate and/or arsenate can be conventionally formed by processes known in the art. When the catalyst comprises the substantially insoluble molybdenum and/or tungsten and the substantially insoluble inorganic metal phosphate and/or arsenate, the catalyst can be formed through one of several methods. In one method, the molybdenum and/or tungsten is dissolved in an appropriate solvent and the solution is contacted with the inorganic metal phosphate and/or arsenate. The resulting solid material is removed from the mixture and any remaining solvent is removed, such as by evaporation. In another method, a mixture of the molybdenum and/or tungsten and the inorganic metal phosphate and/or arsenate is calcined at high temperatures, which can be at a temperature up to the melting point of the materials, to produce the desired catalyst. The catalyst can also be formed by depositing the molybdenum and/or tungsten from the vapor phase by condensation on the support or alternatively, melting the molybdenum and/or tungsten and depositing the molten material onto the inorganic metal phosphate and/or arsenate. In some embodiments of the catalyst, the formed catalyst may be heated to near the melting point of the metal phosphate and/or arsenate to fix the molybdenum and/or tungsten on the support. Whether such treatment is needed or not is dependent on the specific metal present. An in situ method of forming the catalyst can also be used, in such a method, the molybdenum and/or tungsten which is soluble in the olefin-hydroperoxide reaction mixture is added in low concentrations. The inorganic metal phosphate and/or arsenate is then charged to the reaction mixture. The molybdenum and/or tungsten deposits onto the metal phosphate and/or arsenate and little or no molybdenum and/or tungsten is found in the reaction products.

The above techniques produce a substantially insoluble, active and selective molybdenum and/or tungsten-metal phosphate and/or arsenate catalyst or alternatively, a substantially insoluble, inorganic metal phosphate and/or arsenate used in conjunction with a soluble molybdenum and/or tungsten material for the epoxidation of an olefin with a hydroperoxide.

The molybdenum and/or tungsten content of the catalyst will vary with the catalyst preparation technique and with the metal associated with the phosphate and/or arsenate. However, the quantity of molybdenum needed for a given rate of reaction will generally be less, and in many cases substantially less, than that required without the use of the metal phosphate and/or arsenate. The ratio of moles of molybdenum and/or tungsten to moles of hydroperoxide useful in the epoxidation of the olefins can vary from about $10^{-8}:1$ to about $0.5:1$ with the preferred ratio varying from about $10^{-5}:1$ to about $0.05:1$. The ratio of moles of molybdenum to moles of olefin in the reation are about the same as those for the hydroperoxide. The ratio of moles of olefin to moles of hydroperoxide can vary from about $50:1$ to about $1:10$ with the preferred ratio being about $20:1$ to about $1:2$.

The inorganic metal phosphates useful in the present invention, whether combined with the substantially insoluble molybdenum and/or tungsten or used with a soluble molybdenum and/or tungsten, can be the ortho, meta, or pyrophosphate, as well as mixed phosphates. Further, the catalyst can have more than one metal. At the present time, the most preferred inorganic metal phosphates are aluminum metaphosphate, iron phosphate and zinc phosphate. Other phosphate compounds of these metal cations or mixtures of two or more of these metal cations may also be useful in the process of the present invention. Metals other than those listed above that may also be useful in the catalyst and include those from Groups I to III, VIIb, and VIII of the periodic table of elements. Preferred metals include barium, calcium, copper, indium, lanthanum and the other rare earth elements, manganese, mercury, nickel, potassium, silver, sodium, and thalium.

Certain mixtures of metals, such as ferric lithium phosphate, ferric potassium phosphate and aluminum sodium phosphate are also preferred as catalytic enhancers. Many of the metal phosphates are so effective as catalyst promoters that the quantity of soluble molybdenum and/or tungsten necessary with the more active metal phosphates can be 100 parts per million or lower.

Generally the molybdenum and/or tungsten is used as a compound. Soluble molybdenum compounds include molybdenum oxides, molybdates such as sodium, potassium or ammonium molybdate, polymolybdates such as ammonium heptamolybdate, heteropolymolybdates such as phosphomolybdic acid, molybdenum halides and oxyhalides such as molybdenum pentachloride and molybdenum oxytrichloride and the complex molybdenum compounds of amines, alcohols, carboxylic acids, and carbonyls such as molybdenum hexacarbonyl, molybdenum acetylacetonate, glycolates of molybdenum, and molybdenum salts of organic acids. Chelates of molybdenum, such as molybdenum EDTA complex, and diethylene triamine complex, are also useful. Other useful molybdenum compounds include molybdenum tert.-butylate, molybdenum salts of organic acid such as molybdenum octanoate, molybdenum naphthenate, and molybdenum neodecanoate.

Useful tungsten compounds include the tungstates, polytungstates, tungsten oxides, heteropolytungstates, tungsten halides, tungsten oxyhalides, and the complex tungsten compounds of amines, alcohols, carboxylic acids and carbonyls.

Inorganic metal arsenates have also been found to enhance the catalytic properties of both soluble and substantially insoluble molybdenum and/or tungsten. Various metal arsenates are known, and useful one will contain metals of Groups I to III, VIIb and VIII of the periodic table of elements.

Active catalytic combinations of molybdenum and/or tungsten, and an inorganic metal phosphate and/or arsenate, wherein the molybdenum and/or tungsten is substantially insoluble in the reaction mixture can be formed by several methods which generally involve bringing the molybdenum and/or tungsten compound into effective contact with the inorganic metal phosphate and/or arsenate. Such methods include the treatment of the inorganic metal phosphate and/or arsenate with a solution of a molybdenum and/or tungsten compound, vapor deposition of the molybdenum and/or tungsten compound on the inorganic metal phosphate and/or arsenate, mechanical milling or mixing of the molybdenum compound and/or tungsten compound with the inorganic metal phosphate and/or arsenate, precipitation or co-precipitation of the molybdenum and/or tungsten compound with the inorganic metal phosphate and/or arsenate is also useful. Heat treatment or calcining of the formed catalyst is often useful in forming a useful catalyst and for some combinations calcining is necessary.

Generally. it has been found that low concentrations of molybdenum and/or tungsten combined with the inorganic metal phosphate and/or arsenate is useful as the catalyst, even though the effective catalytic amount of the molybdenum and/or tungsten varies with the type of inorganic metal phosphate and/or arsenate used. Amounts far less than 1 weight percent molybdenum and/or tungsten combined with the inorganic metal phosphate and/or arsenate have been found to be effective catalysts. In general, though, the greater the amount of molybdenum and/or tungsten present, the greater the catalytic effect of the catalyst. The maximum molybdenum and/or tungsten concentration in the catalyst may be considered the point at which the molybdenum and/or tungsten leaches excessively from the catalyst into the reaction mixture. This maximum molybdenum and/or tungsten concentration varies with the metal phosphate and/or arsenate used, with the method of preparation of the catalyst, and with the composition of the olefin-hydroperoxide reaction mixture. A concentration of molybdenum and/or tungsten in the catalyst of 3 to 6 percent may be readily achieved with many metal phosphates and/or arsenates and may be increased to greater than 9 percent in some cases while still maintaining a catalyst which does not leach molybdenum and/or tungsten during the epoxidation reaction.

A high concentration of molybdenum and/or tungsten relative to the inorganic metal phosphate and/or arsenate while still maintaining the insolubility of the molybdenum and/or tungsten in the reaction mixture, is desirable in a highly active catalyst. This can be achieved by using certain methods, one of these methods is the use of mixed phosphates, such as iron and potassium phosphates, or aluminum and sodium phosphates. Another method involves the pretreatment of the inorganic metal phosphate with other metals such as calcium, barium, sodium, lithium and zinc. Post treatment of the catalyst with the same metals and the use of a phosphoric acid solution of molybdenum and/or tungsten compounds to prepare the catalyst combinations can also be used. In many cases, the use of calcining temperatures of from about 100° C. to about 900° C., preferably of from about 300° C. to 800° C. have also been found to be useful.

The substantially insoluble inorganic metal phosphate and/or arsenate preferably has sufficient structural strength so as not to physically degrade during the epoxidation reaction and during any subsequent recycling of the catalyst. Further, the inorganic metal phosphate and/or arsenate can preferably conduct heat and tolerate changes in temperature. The inorganic metal phosphate and/or arsenate, whether combined with molybdenum and/or tungsten or not, can also be combined with a suitable inert carrier, such as silica gel, silicon carbide, zirconia, alumina, and natural and synthetic zeolites. The surface area of the inorganic metal phosphate and/or arsenate whether combined with a carrier or not can vary widely, from less than about 1 square meter per gram to more than about 700 square meters per gram. The preferred surface area is toward the lower end of the above range.

The epoxidation reaction can be carried out at a temperature from about 20° C. to about 200° C. with a preferred range being from about 70° C. to 150° C. The reaction can also be carried out at a pressure of about 0.1 to about 340 atmospheres with a preferred range being from about 0.5 to about 170 atmospheres. The process can be practiced either in batch or in continuous reaction processes, such as those set forth in the examples.

The process of the present invention is generally applicable to the epoxidation of any organic compound having at least one unsaturated carbon to carbon double bond. Preferably, the olefins will have from about 3 to about 40 carbon atoms and can be mono, di, and polyolefins; acylic, linear, branched or cyclic olefins; mono, di, tri and poly-substituted olefins; and olefins substituted with various functional groups such as alcohols, ethers, esters, and nitro groups. Examples of useful olefins include propylene, butylene, isobutylene, the pentenes, the hexenes, the octenes, the dodecenes, the cyclohexenes, butadiene, styrene, aryl substituted alkylolefins, cyclohexenol, diallyl ether and methyl oleate. Preferred olefins include 1-butylene, alpha and internal olefins having 5 to 20 carbon atoms such as 1-hexene, 1-octene, dodecene, and 1,11-dodecadiene, and cyclic olefins having 5 to 12 carbon atoms such as cyclohexene and vinylcyclohexene.

The hydroperoxide reactant used in the process of the present invention generally has the formula:

ROOH wherein R is an organic radical. Preferably, R is a substituted or unsubstituted alkyl, cycloalkyl, arylalkyl, arylalkenyl, hydroxyarylalkyl, cycloalkenyl, hydroxycycloalkyl, heterocyclic and the like. R can also contain halogen atoms and oxygen or oxygen containing functional groups. Useful hydroperoxides include cumene hydroperoxide, 1-phenyl ethyl hydroperoxide, cyclohexanone peroxide, methyl ether ketone peroxide, tert.-butylhydroperoxide, and the like.

Generally, the mole ratio of olefinic groups in the olefin to the hydroperoxide can vary within the range of about 0.5:1 to about 100:1 with the range of about 1:1 to about 20:1 being preferred. The reaction can be carried out in the presence of a solvent such as ethylbenzene, cumene, cyclohexanone and butylene but preferably a solvent is not used, with the reaction simply taking place by contacting the hydroperoxide, the olefin, and the catalyst within the desired temperature and pressure range. After the epoxidation is completed, the insoluble catalyst can be conventionally separated from the reaction mixture and recycled for further use.

The following examples are given to illustrate the invention but are not meant to limit or otherwise restrict the invention. In the examples, all concentrations in parts per million are by weight.

EXAMPLE I

To a 50 milliliter glass reactor equipped with a distillation head and a reflux condenser was charged about 16.8 grams of 1-octene which had been stirred with molybdenum acetylacetonate and contained less than about 1.7 parts per million molybdenum, and 5.0 grams of 90 percent tertiary butyl hydroperoxide (TBHP). The reactor was then flushed with nitrogen and heated under reflux for about 5 hours with stirring. Accumulated water was drained and the reactor effluent was filtered to free it from solids. The effluent was analyzed for remaining hydroperoxide by iodometric titration, for octene oxidation products by gas-liquid chromatography, and for soluble molybdenum by atomic absorption spectroscopy. The results of this reaction are set forth in Table I.

EXAMPLE II

To the reaction mixture of Example I was added about 1 gram of zinc phosphate ($Zn_3(PO_4)_2 \cdot XH_2O$) and the reaction was carried out as in Example I. The results of this reaction are set forth in Table I.

EXAMPLE III

To the reaction mixture of Example I was added about 1 gram of aluminum oxide ($Al_2O_3$). The reaction was carried out as in Example I and the results are set forth in Table I.

From the results of Examples I–III it can be seen that the small quantity of soluble molybdenum present in the reaction mixture in Example I, less than about 1.7 parts per million, was not sufficient to catalyze the reaction of the olefin and hydroperoxide, with the yield of oxide being only 3.3 percent. However, in Example II it can be seen that the with addition of the zinc phosphate the catalytic effect of the small quantity of molybdenum present in the solution was enhanced since the yield of the oxide increased to 23.2 percent. From Example III it can be seen that the zinc phosphate was the effective agent in enhancing the molybdenum activity, since the addition of alumina instead of zinc phosphate produced a yield of oxide of only 1.7 percent.

EXAMPLES IV-VII

To a 50 milliliter reactor equipped with a distillation head and a reflux condenser was added about 33.6 grams (except in Example IV where it was about 16.8 grams) of 1-octene, 5.0 grams of 90 percent tertiary butyl hydroperoxide (TBHP) and 1 gram of an inorganic metal phosphate which was substantially insoluble in the reaction mixture. No molybdenum or tungsten was used. The specific metal phosphate used in each example is set forth in Table I. The reactor was flushed with nitrogen and the reaction mixture was heated and maintained at a reflux temperature for about 5 hours with stirring. Accumulated water was drained. The reaction mixture was then filtered to free it from solids, and analyzed for remaining hydroperoxide by iodometric titration, for octene oxidation products by gas liquid chromotography, and for soluble molybdenum by atomic absorption spectroscopy. The results are set forth on Table I.

From the results of Examples IV-VII wherein the yield of oxide is extremely low, it can be seen that inorganic metal phosphates by themselves do not catalyze the epoxidation of an olefin by hydroperoxide.

EXAMPLES VIII-XIII

Into a 100 ml glass reactor was charged about 33.6 grams of 1 octene, 10 grams of 90 percent tertiary butyl hydroperoxide (TBHP), 3.73 grams of n-undecane (internal standard), 6.0 grams of tertiary butyl alcohol containing 38 parts per million molybdenum from molybdenum carbonyl ($Mo(CO)_6$), or tertiary butyl alcohol containing molybdenum from ammonium heptamolybdate in Example XII, and, except for Example VIII, 1 gram of a phosphate as set forth in Table I.

The starting concentration of molybdenum in Examples VIII-XI and XIII was about 2.25 parts per million and in Example XII it was about 4.3 parts per million. The reactor was flushed with nitrogen and then was heated at a reflux temperature with stirring for about 5 hours. Small amounts of azeotroped water were drained as they accumulated. The fluid was analyzed for remaining hydroperoxide by iodometric titration, for octene oxidation products by gas-liquid chromotography, and for soluble metals by atomic absorbtion spectroscopy. The results are set forth in Table I.

By comparing the results of the phosphate promoted epoxidations (Examples IX to XIII) against those without the phosphate promoter (Example VIII) set forth in Table I, it can be seen that zinc phosphate, iron phosphate and aluminum metaphosphate all promote the activity of the molybdenum catalysts producing higher observed yields and improving the selectivities of the epoxidation reaction.

EXAMPLE XIV

A 100 milliliter reactor equipped with a distillation head and a reflux condenser was charged with about 31.6 grams of cyclooctene, 20.8 grams of cumene hydroperoxide, 5.8 grams of a tertiary butyl alcohol solution containing 38 parts per million molybdenum from ammonium heptamolybdate, and 0.62 grams of zinc phosphate. The mixture was stirred and refluxed for about 5 hours and then analyzed for hydroperoxide and oxides. The conversion of the hydroperoxide was about 99.8 percent and the cyclooctene oxide yield was near quantitive with selectivity to cyclooctene oxide (basis other oxidation products) of 99.5 percent. The results of this experiment demonstrate that the process of present invention is also applicable to cycloolefins.

EXAMPLE XV

To a one liter autoclave was charged about 100 grams of a solvent, here ethylbenzene, 50 grams of 90 percent tertiary butyl hydroperoxide, 11 grams of tertiary butanol containing 38 parts per million molybdenum, and 3 grams of zinc phosphate. To this mixture was charged about 168 grams of propylene. The contents were then stirred and heated to about 100° C. for about three hours. After cooling, the autoclave was vented and a gas and liquid sample were collected. The liquid sample contained about 4.11 percent propylene oxide by weight and the gas sample contained about 2.4 percent propylene oxide. This is an about 23 percent yield basis TBHP avialable (65 percent selectivity basis TBHP). The propylene oxide to acetone ratio in this liquid sample was about 41:1. No molybdenum was detected in the effluent solution. This example demonstrates that the process of the present invention is useful for the production of propylene oxide.

EXAMPLE XVI

About 20 grams of sodium metaphosphate ($NaPO_3$) and 48 grams of a solution of ammonium heptamolybdate in water which contained 1.2 percent molybdenum by weight were combined in a glass flask. The water in the slurry was removed under reduced pressure at about 100° C. The resulting powder was used as a catalyst directly or calcined at about 400° C. and then used as a catalyst.

To a 100 milliliter glass reactor equipped with a distillation head and a reflux condenser was charged about 1 gram of the calcined catalyst made as in the above paragraph, 33.6 grams of 1-octene, 3.73 grams of n-undecane (internal standard), and 100 grams of 90 percent tertiary butyl hydroperoxide. The mixture was stirred and heated at reflux for about five hours. Analysis of the filtrate from the reaction mixture showed a hydroperoxide conversion of 61 percent with a selectivity to octene oxide of 91 percent. No molybdenum could be detected in the filtrate with the detection limit of the apparatus being about 0.4 parts per million by weight of molybdenum.

EXAMPLES XVII TO XLII

A catalyst was formed by combining in a glass flask about 20 grams of the metal phosphate listed for each example in Table II and about 50 grams of an ammonium heptamolybdate solution in water. The water in the resulting slurry was removed under reduced pressure at about 100° C. The resulting powder was calcined at about the temperature listed in the fourth column of Table II and contained about the percentage of molybdenum indicated in the third column.

About one gram of each of the catalysts formed in the preceeding paragraph, 33.6 grams 1-octane, 3.73 grams n-undecane and 10 grams of 90 percent tertiary butyl hydroperoxide were added to a 100 ml. reactor equipped with a distillation head and a reflux condenser. The mixture was stirred and heated at reflux for about 5 hours. The analysis of the filtrate, including the hydroperoxide conversion in mole percent, the selectivity to epoxide (based on hydroperoxide converted) in percent, the molybdenum in the effluent in parts per million and the detection limit for molybdenum in parts per million for each catalyst are set forth on Table II.

A review of the results of Examples XVII through XLII set forth in Table II discloses that there are many metal phosphates which enhance the catalytic effects of molybdenum, whether the molybdenum is soluble or not. Such enhancement is shown by comparing the results of Examples I or VIII of Table I which use soluble molybdenum with Examples XVII through XLII which use added inorganic metal phosphates and display enhanced catalytic activity over molybdenum used alone.

EXAMPLE XLIII

A tungsten-ferric phosphate catalyst containing about 2.3 percent tungsten was prepared by evaporating a solution of ammonium paratungstate in the presence of ferric phosphate. The resulting material was calcined for about two hours at about 600° C. The calcined catalyst was used as in the second paragraph of Example XVI and was found to give a 49 percent conversion of hydroperoxide with a selectivity to the octene oxide of 79 percent based on converted hydroperoxide. No tungsten could be detected in the filtered reaction mixture. This example shows that the catalytic activity of tungsten-metal phosphate catalyst is enhanced by the presence of an inorganic metal phosphate as compared to the known activity of tungsten alone.

EXAMPLE XLIV

An ammonium heptamolybdate solution was evaporated in the presence of aluminum arsenate to give a catalyst containing about 1 percent by weight molybdenum. The arsenate was prepared by precipitation from a mixture of sodium arsenate and aluminum nitrate. The molybdenum-metal arsenate catalyst was calcined for about 19 hours at about 400° C.

The molybdenum-metal arsenate catalyst was used in an epoxidation reaction as in the second paragraph of Example XVI. The use of this catalyst produced a 79 percent conversion of hydroperoxide with a selectivity to octene oxide of 82 percent. No molybdenum could be detected in the filtered reaction mixture with the detection limit of the apparatus being at about 0.31 part per million of molybdenum.

EXAMPLE XLV

A solution of about 5 grams of molybdic acid in 100 milliliters of 10 percent phosphoric acid was thoroughly mixed with 100 grams of ferric orthophosphate. The resulting paste was dried at about 120° C. for about 6 hours, then broken into small chunks and calcined for about 3 hours at about 400° C. and then for about 2.5 hours at about 600° C.

About 2 grams of the catalyst made in the preceeding paragraph was added to a flask. Also added to the flask was about 42 grams of 1-octene, and 12.5 grams of 90 percent tertiary butyl hydroperoxide. The reaction mixture was stirred under reflux condition for about 3 hours. The reaction products were analyzed as described in the previous examples and the results were set forth on Table III.

EXAMPLE XLVI

A solution of about 4 grams molybdic acid in 100 milliliters of a 10 percent phosphoric acid solution was boiled and stirred with 100 grams of aluminum metaphosphate until a thick paste was obtained. The paste was dried and then calcined at about 350° to 425° C. for about 3.5 hours. A 10 gram portion of the calcined catalyst was stirred and heated with a solution of about 225 milligrams of bismuth nitrate ($Bi(NO_3)_2 \cdot 5H_2O$) in 10 milliliters of a 15 percent nitric acid until a thick paste was obtained. The paste was dried, then calcined for about one hour at about 400° C. and then for an additional 1.5 hours at about 600° C. This catalyst was used as in the second paragraph of Example XLV and the results are set forth in Table III.

EXAMPLE XLVII

A solution of about 10 grams of molybdic acid and about 5 grams of potassium hydroxide in about 100 milliliters of water were stirred and heated with about 200 grams of aluminum metaphosphate until a thick paste was obtained. The paste was dried at about 120° C. and then calcined for about 2 hours at about 600° C. The resulting catalyst was used as in the second paragraph of Example XLV and the results are set forth on Table III.

From the results of Examples XLV to XLVII set forth in Table III, it can be seen that molybdenum metal phosphate catalysts made as in Examples XLV to XLVII are able to satisfactorily catalyze the reaction of an olefin and a hydroperoxide to produce an olefin oxide. The yield of oxide and the selectivity towards the olefin oxide (basis the peroxide) being very high and of commercial significance.

EXAMPLE XLVIII

A catalyst was prepared by mixing a solution of about 50 grams of molybdic acid and 500 milliliters of a 10 percent phosphoric acid with 470 grams of ferric orthophosphate. The resulting mixture was dried at about 120° C. and the resulting solid material was calcined for about 2.5 hours at about 400° C. The catalyst was then crushed and sieved. The sieved particles were then recalcined for about 2 hours at about 600° C. and then calcined for about 2 hours at about 800° C. A portion of the catalyst was then placed into a tube to form a continuous reactor.

A mixture of propylene, tertiary butyl hydroperoxide, and ethylbenzene (the mole ratio of propylene to tertiary butyl hydroperoxide being about 13.5) was past through the continuous reactor containing the catalyst made in the preceeding paragraph. The reactor was maintained at a temperature of about 120° C. and at a pressure of about 450 psig with the mixture passing through the reactor at a liquid hourly space velocity of about 3.14. Propylene oxide was produced at a 96 percent selectivity based on propylene and a 49 percent selectivity based on hydroperoxide. Conversion of the hydroperoxide was about 28 percent.

The above Examples illustrate the use of phosphates and arsenates as catalytic enhancers for molybdenum and/or tungsten. Those catalysts which comprise a molybdenum-metal-phosphate compound, wherein the molybdenum is substantially insoluble in the reaction mixture is an advance over the prior art wherein the molybdenum generally leached into the reaction mixture and thus rapidly inactivated the supposedly heterogenous catalyst. In the process of the present invention, such leaching does not occur, which greatly extends the useful life of the heterogenous molybdenum catalyst. Further, wherein the inorganic metal-phosphate and/or arsenate is used as an enhancer for the molybdenum and/or tungsten, such enhancement greatly increases the catalytic activity of the molybdenum and/or tungsten permitting the use of smaller quantities of molybdenum and/or tungsten and permitting a more rapid reaction rate resulting in a greater commercial benefit.

The above Examples are meant only to illustrate the process of the present invention and not limit the invention in any way which invention was set forth in the following claims.

TABLE I

| | | | | | | | Selectivity In Percent Basis | | Grams Of Octene Originally In Reaction Mixture | Moles Of Octene Per Moles Of TBHP |
|---|---|---|---|---|---|---|---|---|---|---|
| Example | Catalyst | Mo In PPM Originally Added To Reaction Mixture | Lower Detection Limit Of Mo In PPM | Grams Of Metal Phosphate | Yield Oxide (Basis TBHP) In Percent | Conversion Of TBHP In Percent | TBHP | Oxide | | |
| | | | | SOLUBLE MOLYBDENUM | | | | | | |
| I | Mo Acetylacetonate | Less than 1.7 | Less than 1.02 | 0 | 3.3 | — | | 52.8 | 16.8 | 3 |
| II | Mo Acetylacetonate + $Zn_3(PO_4)_2 \cdot XH_2O$ | Less than 1.7 | Less than 1.05 | 1 | 23.2 | — | 99.1 | 85.3 | 16.8 | 3 |
| III | Mo Acetylacetonate + $AL_2O_3$ | Less than 1.7 | Less than 0.94 | 1 | 1.7 | | 47.4 | 40.1 | 16.8 | 3 |
| IV | $Zn_3(PO_4)_2$ Cal at 400° C. | 0 | — | 1 | 2.65 | | | 71.8 | 33.6 | 3 |
| V | $FePO_4 \cdot XH_2O$ | 0 | — | 1 | 3.1 | — | | 76.9 | 33.6 | 3 |
| VI | $Fe_3(PO_4)_2 H_2O$ | 0 | — | 1 | 2.2 | 26.8 | 8.21 | 67.9 | 33.6 | 3 |
| VII | $Al(PO_3)_3$ | 0 | — | 1 | 1.15 | 4.6 | 25.0 | 52.0 | 16.8 | 3 |
| VIII | $Mo(CO)_6$ | About 2.25 | Less than 2.7 | 0 | 22.8 | 40.5 | 56.2 | 88.1 | 33.6 | |
| IX | $Mo(CO)_6$ + $Zn_3(PO_4)_2$ Cal at 400° C. | About 2.25 | Less than 2.7 | 1 | 35.5 | 49.6 | 71.5 | 91.2 | 33.6 | |
| X | $Mo(CO)_6$ + $Zn_2(PO_4)_2 \cdot 2.5H_2O$ | About 2.25 | Less than 2.7 | 1 | 35.2 | 48.1 | 73.2 | 90.2 | 33.6 | |
| XI | $Mo(CO)_6$ + $FePO_4 \cdot XH_2O$ | About 2.25 | Less than 2.7 | 1 | 38.8 | 44.9 | 86.4 | 90.9 | 33.6 | |
| XII | $(NH_4)_6 Mo_7O_{24}$ + $Al(PO_3)_3$ | About 4.3 | Less than 0.22 | 1 | 23.8 | 23.3 | 102 | 87.9 | 33.6 | |
| XIII | $Mo(CO)_6$ + ZnO | About 2.25 | Less than 2.7 | 1 | 3.00 | 19.7 | 15.2 | 37.7 | 33.6 | |

TABLE II

| EXAMPLE | METAL PHOSPHATE | PERCENT Mo IN CATALYST | CALCINING TEMPERATURE °C. OF METAL PHOSPHATE | HYDROPEROXIDE CONVERSION MOLE PERCENT | SELECTIVITY TO EPOXIDE (BASIS TBHP) | DETECTION LIMIT OF Mo IN PPM | Mo IN EFFLUENT IN PPM |
|---|---|---|---|---|---|---|---|
| XVII | $Li_3PO_4$ | 2 | 400 | 66 | 60 | 0.31 | — |
| XVIII | $Li_3PO_4$ | 1 | 550 | 71 | 81 | 1.86 | — |
| XIX | $Ag_3PO_4$ | 1 | 550 | 25 | 84 | 0.82 | — |
| XX | $NaH_2PO_4$ | 1 | 550 | 65 | 80 | 0.99 | — |
| XXI | $LaPO_4$ | 1 | 550 | 16 | 47 | 0.83 | — |
| XXII | $Ni_3(PO_4)_2$ | 1 | 450 | 83 | 86 | 1.2 | — |
| XXIII | $Ba_3(PO_4)_2$ | 1 | 450 | 6 | 39 | 1.3 | — |
| XXIV | $(NaPO_3)_n$ Sodium Metaphosphate | 1 | 400 | 52 | 73 | 0.18 | — |
| XXV | $FePO_4 \cdot Li_3PO_4$ (1) | 1 | 400 | 78 | 95 | 0.19 | — |
| XXVI | $Zn_3(PO_4)_2$ | 1 | 400 | 93 | 82 | 0.4 | — |
| XXVII | Sodium Zinc Phosphate (2) | 1 | 425 | 21 | 34 | 0.3 | — |
| XXVIII | 4.2:10 $FePO_4:K_3PO_4$ | 3.9 | 400 | 54 | 66 | 0.19 | — |
| XXIX | 4.2:10 $FePO_4:K_3PO_4$ | 4 | 600 | 61 | 82 | 0.18 | — |
| XXX | $AlPO_4$ (3) | 1 | 100 | 91 | 85 | 0.18 | — |
| XXXI | $AlPO_4$ (3) | 1 | 550 | 62 | 88 | 1.24 | — |
| XXXII | $FePO_4$ | 1 | 600 | 99 | 73 | 1.67 | — |
| XXXIII | $FePO_4$ | 1 | 100 | 97 | 87 | 0.96 | — |
| XXXIV | $Al(PO_3)_3$ | 1 | 450 | 83 | 83 | 1.18 | — |

TABLE II-continued

| EXAMPLE | METAL PHOSPHATE | PERCENT Mo IN CATALYST | CALCINING TEMPERATURE °C. OF METAL PHOSPHATE | HYDROPEROXIDE CONVERSION MOLE PERCENT | SELECTIVITY TO EPOXIDE (BASIS TBHP) | DETECTION LIMIT OF Mo IN PPM | Mo IN EFFLUENT IN PPM |
|---|---|---|---|---|---|---|---|
| XXXV | Commercial Aluminum Phosphate Containing 17% Sodium | 2 | 450 | 57 | 75 | 2.3 | — |
| XXXVI | $CuP_2O_7$ | 1 | 500 | 66 | 84 | 1.3 | — |
| XXXVII | $CaHPO_4$ | 1 | 450 | 88 | 85 | — | — |
| XXXVIII | $Ca_3(PO_4)_2$ | 1 | 700 | 80 | 85 | — | 0.58 |
| XXXIX | $MnPO_4$ | 1 | 400 | 74 | 38 | — | 2.26 |
| XL | $CePO_4$ | 1 | 575 | 91 | 79 | — | 61 |
| XLI | $Co_3(PO_4)_2$ | 1 | 500 | 97 | 77 | — | 19.7 |
| XLII | $Mg_2P_2O_7$ | 1 | 450 | 99 | 83 | — | 31 |

(1) Fused at 1100° C.
(2) Commercial Sample
(3) From $Al(NO_3)$ and $Na_3PO_4$

TABLE III

| EXAMPLE | METAL PHOSPHATE | HYDROPEROXIDE CONVERSION IN PERCENT | SELECTIVITY TO OCTENE OXIDE (BASIS HYDROPEROXIDE) IN PERCENT | DETECTION LIMIT OF Mo IN PPM | Mo IN EFFLUENT IN PPM |
|---|---|---|---|---|---|
| XLV | Ferric Orthophosphate | 64 | 94 | 0.5 | — |
| XLVI | Aluminum Metaphosphate | 80 | 95 | 0.07 | — |
| XLVII | KOH + Aluminum Metaphosphate | 82 | 89 | 0.40 | — |

What is claimed is:

1. A method for the preparation of an epoxide comprising the step of reacting an olefin selected from the group consisting of 1-butylene, propylene, alpha and internal olefins having from 5 to 20 carbon atoms, with a hydroperoxide in the presence of a catalyst; said catalyst comprising molybdenum and/or tungsten, and an inorganic metal phosphate and/or arsenate wherein at least said inorganic metal phosphate and/or arsenate is substantially insoluble in the olefin-hydroperoxide reaction mixture, and said metal portion of said inorganic metal phosphate and/or arsenate is selected from the group consisting of aluminum, zinc, and mixtures of these metals.

2. The method of claim 1, wherein all portions of said catalyst are substantially insoluble in the olefin-hydroperoxide mixture.

3. The method of claim 1, wherein said hydroperoxide is selected from the group consisting of alkyl hydroperoxides and aryl substituted alkyl hydroperoxide.

4. The method of claim 1, wherein said hydroperoxide is selected from the group consisting of tertiary butyl hydroperoxide, cumene hydroperoxide, and 1-phenyl ethyl hydroperoxide.

5. The method of claim 1, wherein said olefin and said hydroperoxide are reacted at temperature between about 70° C. and 150° C.

6. The method of claim 1, wherein said olefin and said hydroperoxide are reacted at a pressure between about 0.5 and about 170 atmospheres.

7. The method of claim 1, wherein the ratio of olefin groups in said olefin to said hydroperoxide is within the range of from about 1:2 to about 20:1.

8. The method of claim 1, wherein the concentration of soluble molybdenum in the reaction mixture of said olefin with said hydroperoxide is less than about 100 parts per million.

9. The method of claim 1, wherein the concentration of soluble molybdenum in the reaction mixture of said olefin with said hydroperoxide is less than about 10 parts per million.

10. A method for the preparation of an epoxide comprising the step of reacting an olefin selected from the group consisting of 1-butylene, propylene, alpha and internal olefins having from 5 to 20 carbon atoms, with a hydroperoxide in the presence of a catalyst, said catalyst comprising a molybdenum metal phosphate, and wherein said catalyst is substantially insoluble in the olefin-hydroperoxide mixture and said metal is selected from the group consisting of aluminum, zinc, and mixtures of these metals.

11. The method of claim 10, wherein the concentration of soluble molybdenum in the reaction mixture of said olefin with said hydroperoxide is less than about 10 parts per million.

12. The method of claim 10, wherein said catalyst was calcined prior to being used.

13. A method for the preparation of an epoxide comprising the step of reacting an olefin selected from the group consisting of 1-butylene, propylene, alpha and internal olefins having from 5 to 20 carbon atoms, with a hydroperoxide in the presence of a dissolved molybdenum compound and an inorganic metal phosphate, which inorganic metal phosphate is substantially insoluble in the olefin hydroperoxide mixture, and said metal is selected from the group consisting of aluminum, zinc, and mixtures of these metals.

* * * * *